United States Patent
Nowlin

(10) Patent No.: US 8,771,608 B2
(45) Date of Patent: Jul. 8, 2014

(54) SUBSTANCE DETECTING APPARATUS

(76) Inventor: Timothy Lee Nowlin, Savannah, TN (US)

( * ) Notice: Subject to any disclaimer, the term of this patent is extended or adjusted under 35 U.S.C. 154(b) by 433 days.

(21) Appl. No.: 13/317,704

(22) Filed: Oct. 26, 2011

(65) Prior Publication Data

US 2013/0109104 A1    May 2, 2013

(51) Int. Cl.
- *G01N 21/75* (2006.01)
- *A61B 5/145* (2006.01)
- *G01N 33/543* (2006.01)
- *G01N 33/94* (2006.01)

(52) U.S. Cl.
CPC ............ *A61B 5/14* (2013.01); *G01N 33/543* (2013.01); *G01N 33/94* (2013.01)
USPC ........... 422/409; 422/401; 422/404; 422/430; 422/500

(58) Field of Classification Search
CPC ......... A61B 5/14; G01N 33/543; G01N 33/94
USPC ........................ 422/401, 404, 409, 430, 500
See application file for complete search history.

(56) References Cited

U.S. PATENT DOCUMENTS 4,318,414 A * 3/1982 Schuster et al. ............... 600/572
7,299,081 B2 * 11/2007 Mace et al. .................... 600/345

FOREIGN PATENT DOCUMENTS

WO         WO 97/33519        *  9/1997

* cited by examiner

*Primary Examiner* — Lyle Alexander
(74) *Attorney, Agent, or Firm* — Donald R. Schoonover

(57) ABSTRACT

An apparatus for using sensors having test strip with sheaths surrounding sensitive area configured to detect certain substance in a liquid test specimen includes a carrier having spaced-apart openings to frictionally hold the sensors, a loading portion to insert the sensors through the openings and to displace the sheaths thereby exposing predetermined lengths of the sensitive areas of the sensors, a testing portion including a container for containing a test specimen as only specified lengths of the predetermined lengths of the sensitive areas of the sensors are submerged in the test specimen, and an extracting portion structured and configured to receive the carrier with the plurality of said sensors inserted therethrough, the extracting portion having a comb-like structure for displacing the sheaths to return them to their stowed configurations and to eject the sensors from the carrier.

9 Claims, 4 Drawing Sheets

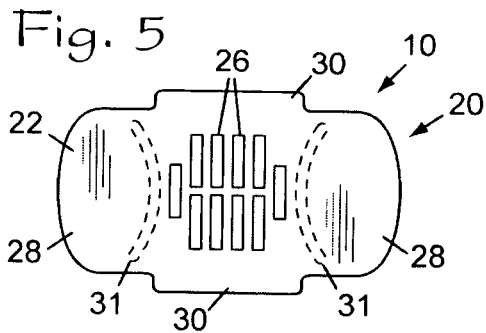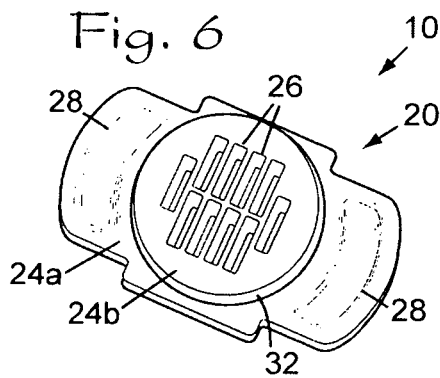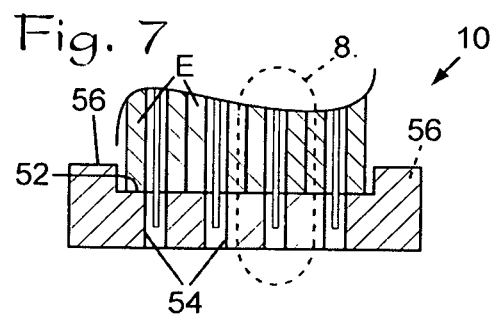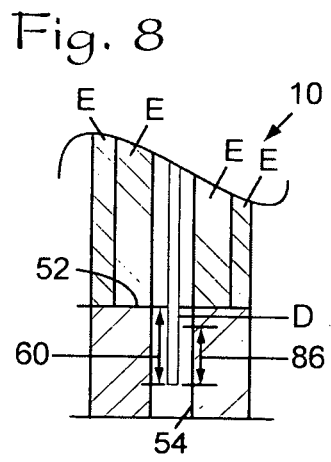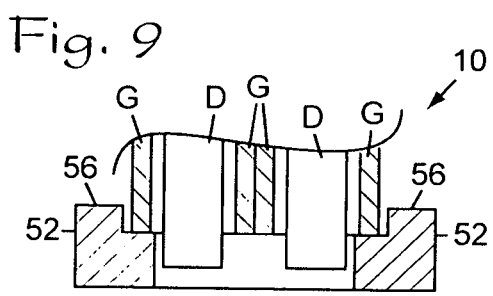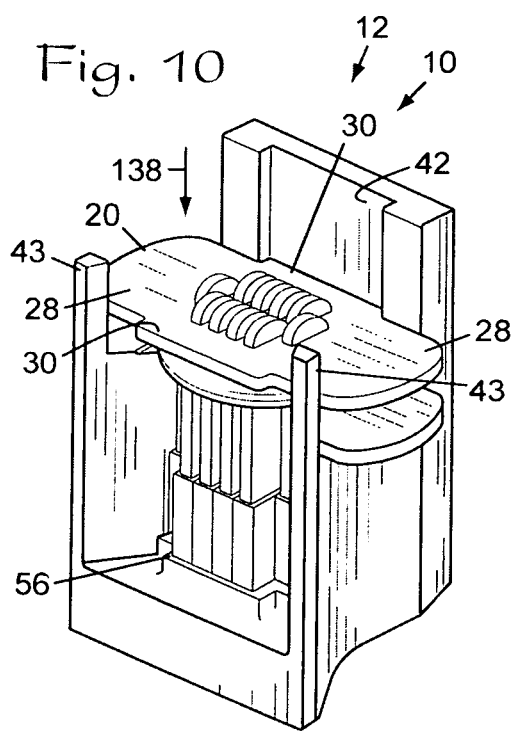

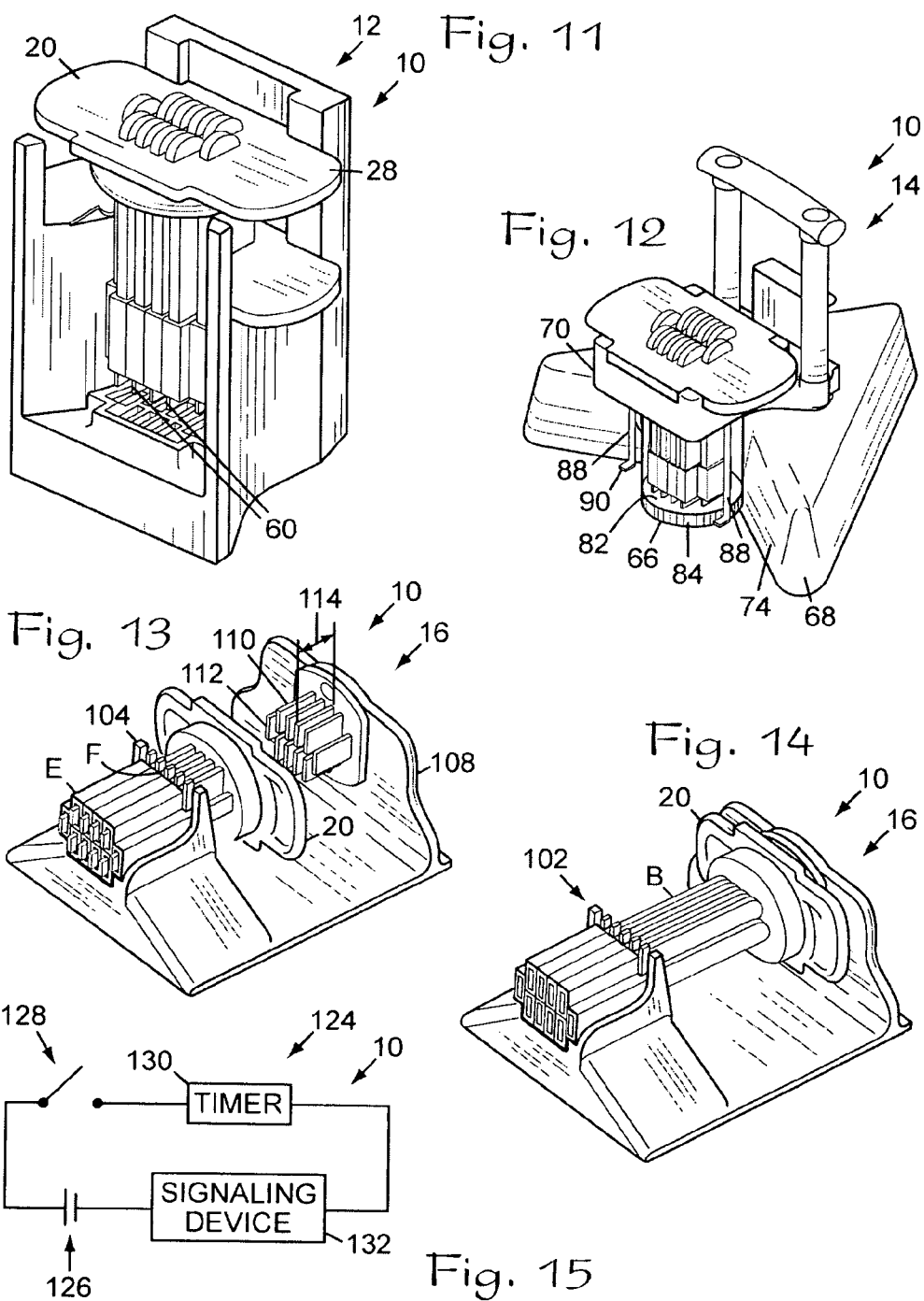

SUBSTANCE DETECTING APPARATUS

BACKGROUND OF THE INVENTION

1. Field of the Invention

The present invention relates to apparatii for detecting the presence of various substances and, more particularly without limitation, to apparatii for detecting the presence of certain controlled substances in a liquid media.

2. Description of the Related Art

A common need in today's societies is the ability to at least qualitatively determine whether certain substances are present in a test specimen. One such determination exists when an individual is suspected of having illegally ingested a controlled substance. Since kidneys are adept at extracting the remnants of most illicit drugs from a bloodstream, a common procedure involves obtaining a urine specimen from a suspect. Various methods exist for determining the presence of illicit drugs in the urine specimen.

One commonly used procedure is to dip the end of a litmus strip in a test specimen wherein the litmus strip is designed to detect the presence of a particular drug in the specimen. When the end of the litmus strip is dipped in the specimen, the submerged end will exhibit a distinctive color change if the drug is present. If the anticipated drug is not present, the submerged end of the litmus strip will not change color.

A plurality of litmus strips have been developed to detect the presence of various specific drugs in a urine specimen. For example, Branan Medical Corporation of Irvine, Calif. has designed Fastect® II sensors for detecting amphetamines, benzodiazepines, barbituates, cocaine, marijuana (THC), methadone, ecstasy (MDMA), methamphetamines, opiates, oxycodone, phencyclidine (PCP), tricyclic antidepressants, or buprenorphine. Test strips have also been developed to detect the presence of alcohol and/or adulterants such as creatinine, nitrites, oxidizing agents, whizzes, bleach, etc.

Most of the aforementioned sensors have a slidably displaceable protective sheath in a stowed configuration that normally surrounds a sensitive area of its test strip. Typically, the sheath is displaced to expose an end of the sensitive area prior to submerging the end thereof in the test specimen. After the end has been submerged for a specified period of time to thereby allow desired chemical activity and color change to occur if the anticipated substance is present, the end is withdrawn from the specimen and the sheath is displaced to again surround the sensitive area.

It is extremely important to ensure the accuracy and reliability of such a test, and to preserve the results of the test for subsequent verification if necessary. Therefore, non-contamination during the test is absolutely essential. Unfortunately, many of the steps taken during a test with such a test strip may create a basis for challenging the results of the test.

For example, improper handling during various stages of a test could lead to possible contamination and degradation of the validity of the test while:

(a) displacing the protective sheath to expose the sensitive area of the test strip;

(b) inadvertently submerging into the test specimen more or less than the recommended length of the sensitive area of the test strip as specified by the manufacturer of the test strip;

(c) inadvertently allowing the end of the sheath to either touch the surface of, or be partially submerged in, the test specimen wherein urine adheres to the sheath;

(d) inadvertently allowing the sensitive area to be submerged in the test specimen for a longer or shorter period of time than specified by the manufacturer of the test strip; and (e) returning the sheath to its stowed configuration to again protectively surround the sensitive area of the test strip.

If more than one substance may be present in the test specimen, a complete analysis requires that a different test strip designed for each of those substances be submerged in the specimen, which tests are generally conducted sequentially. Each such test requires a similar length of time to properly expose each of the different test strips to the specimen. The more individual tests that must be performed, the longer it takes to complete all of the tests of a given specimen from an individual.

Not uncommonly, when tests need to be conducted for one individual, they also need to be conducted on test specimens taken from several individuals at the same time. Conducting complete tests for each of several individuals obviously would require a substantially longer period of time than it would take to complete tests for only one individual. For example, a company or agency may require all job applicants as a condition of employment, or employees as a condition of continued employment, to successfully pass a drug test. Under those circumstances, tests may need to be performed on a large number of individuals. Unfortunately, the longer the time span between the beginning of such tests and completion of the final determination and memorialization of the test results may raise legitimate concerns regarding potential contamination and reliability of the results.

As a result, several technicians working in an assembly line-like fashion may be used to pass the various strips from one to another in order to reduce the time required to fully complete all tests. In so doing, such handling between technicians may further compromise the integrity of the results.

Therefore, what is needed is an apparatus wherein a technician working alone can simultaneously conduct tests on a test specimen with a plurality of test strips having sensitive areas while the test strips are retained separated from each other and while handling by the technician occurs remotely from the sensitive areas at all times.

What is also needed is an apparatus wherein a technician working alone can simultaneously displace the sheaths of a plurality of test strips to thereby expose predetermined lengths of the sensitive areas thereof from their protective sheaths while the test strips are retained separated from each other and while handling by the technician occurs remotely from the sensitive areas at all times.

What is further needed is an apparatus wherein a technician working alone can simultaneously submerge only lengths of the sensitive areas of a plurality of test strips in a test specimen as specified by the manufacturer of the test strips while the test strips are retained separated from each other and while handling by the technician occurs remotely from the sensitive areas at all times.

What is still further needed is an apparatus which prevents the sheaths of a plurality of test strips from touching the surface of, or being submerged in, the test specimen as the sensitive areas are being submerged in the test specimen to thereby avoid adherence of the test specimen to the sheaths.

What is still further needed is an apparatus wherein a technician is automatically alerted when the time specified by the manufacturer of the strips for emersion of the sensitive areas in the test specimen has transpired.

What is still yet further needed is an apparatus wherein a technician working alone can simultaneously withdraw the sensitive areas of a plurality of test strips from the test specimen while the test strips are retained separated from each other and while handling by the technician occurs remotely from the sensitive areas at all times.

What is still yet further needed is an apparatus wherein a technician working alone can simultaneously displace the sheaths of a plurality of test strips to again surround the sensitive areas while the test strips are retained separated from each other and while handling by the technician occurs remotely from the sensitive areas at all times.

SUMMARY OF THE INVENTION

The improvements of the present invention for an apparatus utilizing a plurality of sensors having test strips with sensitive areas surrounded by slidable sheaths in a stowed configuration wherein the sensitive area of each test strip is configured to detect the presence of a different substance in a liquid test specimen include a carrier having a plurality of spaced-apart openings; a loading portion; a testing portion; an extraction portion; and a timing mechanism.

The loading portion includes a loading platform having a loading platform with an upper surface and a plurality of slots corresponding to the plurality of openings of the carrier. The loading portion also includes a lower wall having a plurality of recesses corresponding to the plurality of slots of the loading platform. A handling end of each sensor is placed upright in each slot of the loading platform and the distal end of that sensor is positioned over the recess in the lower wall corresponding to that slot. The recesses are dimensioned such that the sensitive areas of the test strips can enter the recesses but distal ends of the sheaths cannot enter the recesses.

The upper surface of the loading platform is spaced from the lower wall such that, as the carrier is positioned above the plurality of sensors placed upright in the loading portion and displaced downwardly, the plurality of sensors are caused to be frictionally inserted through the openings of the carrier, and as the carrier is further displaced downwardly until it abuttingly engages the upper surface of the platform, the sheaths of the plurality of sensors are displaced upwardly from their stowed configurations thereby allowing the sensitive areas of the sensors to be extended into respective recesses of the lower wall thereby exposing predetermined lengths of the sensitive areas to extend beyond their protective sheaths.

The testing portion includes a base, a testing platform adjustably mounted to the base, a container alignable with the base, and a gauge element configured to enable a user, in conjunction with the adjustability of the testing platform, to position the testing platform wherein only the specified lengths of the sensitive areas of the plurality of sensors are operatively submerged in the test specimen The extracting portion includes a comb-like element having a plurality of spaced-apart fingers corresponding to respective openings of the carrier, and an end wall with a plurality of studs extending toward the comb-like element and corresponding to respective openings of the carrier. After the fingers of the comb-like element have been inserted between the carrier and the sheaths of the sensors inserted through the openings of the carrier, displacement of the carrier toward the end wall until the studs abut the plurality of sensors inserted through the openings of the carrier causes the fingers of the comb-like element to slidingly displace the sheaths returning them to their stowed configurations, and continued displacement of the carrier toward the end wall until the carrier abuttingly engages the end wall causes the studs to eject the plurality of sensors from the openings of the carrier.

A timing mechanism structured and configured to alert a user when the allotted time for submersion of the specified lengths of the sensitive areas of the test strips in the test specimen has transpired.

PRINCIPAL OBJECTS AND ADVANTAGES OF THE INVENTION

The principal objects and advantages of the present invention include: providing a substance detecting apparatus wherein a technician working alone can simultaneously conduct tests on a test specimen with a plurality of test strips having sensitive areas while the test strips are retained separated from each other and while handling by the technician occurs remotely from the sensitive areas at all times; providing such a substance detecting apparatus wherein a technician working alone can simultaneously displace the sheaths of a plurality of test strips to thereby expose predetermined lengths of the sensitive areas thereof from their protective sheaths while the test strips are retained separated from each other and while handling by the technician occurs remotely from the sensitive areas at all times; providing such a substance detecting apparatus wherein a technician working alone can simultaneously submerge the sensitive areas of a plurality of test strips in a test specimen while the test strips are retained separated from each other and while handling by the technician occurs remotely from the sensitive areas at all times; providing such a substance detecting apparatus which prevents the sheaths of a plurality of test strips from touching the surface of, or being submerged in, the test specimen as the sensitive areas are being submerged in the test specimen to thereby avoid adherence of the test specimen to the sheaths; providing such a substance detecting apparatus wherein a technician working alone can simultaneously withdraw the sensitive areas of a plurality of test strips from the test specimen while the test strips are retained separated from each other and while handling by the technician occurs remotely from the sensitive areas at all times; providing such a substance detecting apparatus wherein a technician working alone can simultaneously displace the sheaths of a plurality of test strips to again surround the sensitive areas while the test strips are retained separated from each other and while handling by the technician occurs remotely from the sensitive areas at all times; and generally providing such a substance detecting apparatus that is easily constructed, reliable in performance, capable of long-lasting life, and particularly well adapted for the proposed usages thereof.

Other objects and advantages of this invention will become apparent from the following description taken in conjunction with the accompanying drawings wherein are set forth, by way of illustration and example, certain but non-limiting embodiments of this invention.

BRIEF DESCRIPTION OF THE DRAWING FIGURES

FIG. 5 is a top plan view of a carrier and, in dashed lines, optional grips thereof, of the substance detecting apparatus.

FIG. 6 is a perspective view of a carrier of the substance detecting apparatus.

FIG. 7 is an enlarged and cross-sectional schematic representation of a rib and recesses of a lower wall taken along line 7-7 of FIG. 2 of the loading portion of the substance detecting apparatus.

FIG. 8 is a further enlarged and schematic representation of detail 8 of FIG. 7.

FIG. 9 is an enlarged and cross-sectional schematic representation similar to FIG. 7 but taken along line 8-8 of FIG. 2 of the loading portion of the substance detecting apparatus.

FIG. 10 is a perspective schematic view of sensors being inserted through openings of the carrier of the substance detecting apparatus.

FIG. 11 is a schematic perspective view of the carrier with sensors depending therefrom being removed from the loading portion of the substance detecting apparatus.

FIG. 12 is a schematic perspective view of the sensors depending into a test specimen in a container of the testing portion of the substance detecting apparatus.

FIG. 13 is a schematic perspective view of the carrier with sensors lowered onto a comb-like element of an extracting portion of the substance detecting apparatus.

FIG. 14 is a schematic perspective view showing sensors being ejected from the carrier by the extracting portion of the substance detecting apparatus.

FIG. 15 is a schematic representation of a timing mechanism of the substance detecting apparatus according to the present invention.

DETAILED DESCRIPTION OF THE INVENTION

As required, embodiments of the present invention are disclosed herein, however, it is to be understood that the disclosed embodiments are merely exemplary of the invention, which may be embodied in various forms. Therefore, specific structural and functional details disclosed herein are not to be interpreted as limiting, but merely as a basis for claims and as a representative basis for teaching one skilled in the art to variously employ the present invention in virtually any appropriately detailed structure.

The present invention is structured and configured to utilize sensors A such as, for example, the Fastect® II sensors as provided by Branan Medical Corporation of Irvine, Calif. Each sensor A includes a handling or upper end B, a litmus-like test strip C secured to the handling end B and having a sensitive area D comprising a special chemical composition designed to detect and react to the presence of a particular substance when that substance is present in a liquid media, and a sheath E having a proximal end F and a distal end G. The sheath E, which surrounds the sensitive area D of the test strip C, is slidably and telescopingly mounted about the handling end B of the sensor A to either be positioned in a stowed position, as shown in FIG. 1, wherein the sheath E protectively surrounds the sensitive area D, or be selectively displaced to expose the sensitive area D as described herein.

Figure 1:
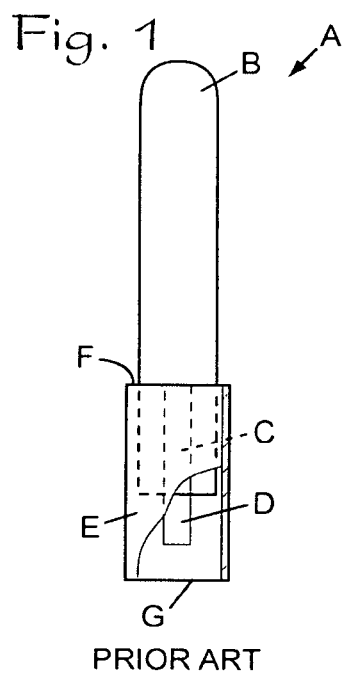
FIG. 1 is a plan view of an exemplary prior art sensor with portions cut away to reveal details thereof, the exemplary sensor utilized by an inventive substance detecting apparatus according to the present invention.
Figure 2:
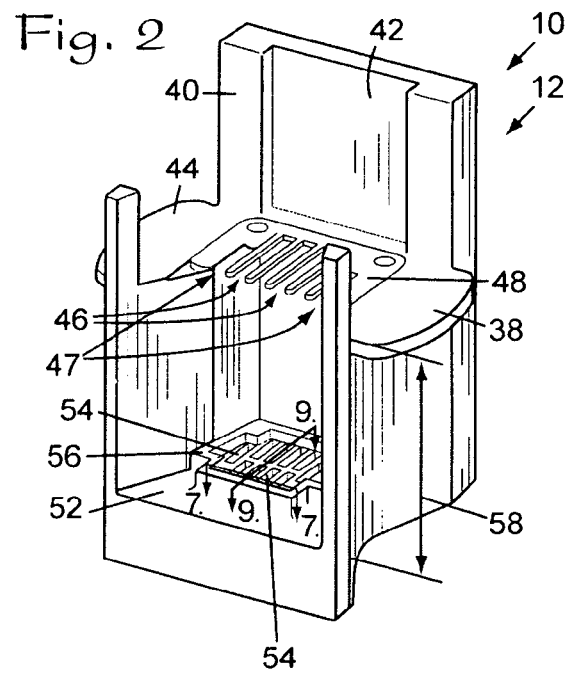
FIG. 2 is a schematic perspective view of a loading portion of the substance detecting apparatus.
Figure 3:
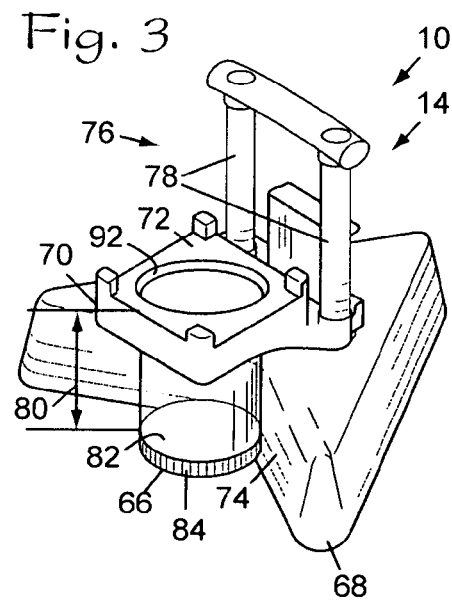
FIG. 3 is a schematic perspective view of a testing portion of the substance detecting apparatus.
Figure 4:
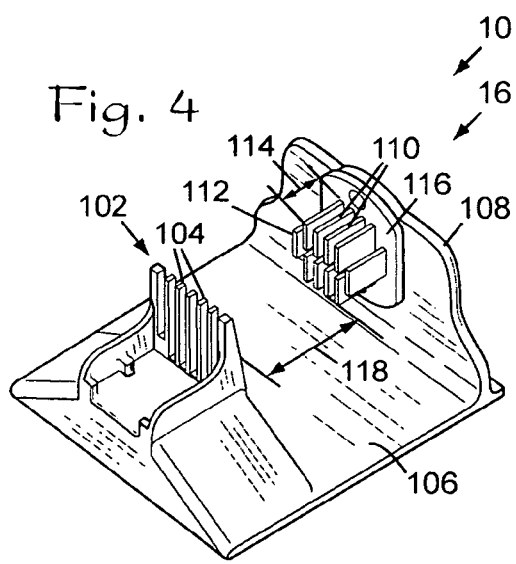
FIG. 4 is a schematic perspective view of an extracting portion of the substance detecting apparatus.

The reference numeral 10 generally refers to an apparatus for utilizing sensors A to detect the presence of certain substances in a liquid media in accordance with the present invention, as shown in FIGS. 1 through 1. The apparatus 10 includes a loading portion 12 as shown in FIGS. 2, 10 and 11; a testing portion 14 as shown in FIGS. 3 and 12; and an extracting portion 16 as shown in FIGS. 4, 13 and 14.

The present invention 10 also includes a carrier 20 having an upper surface 22, lower surfaces 24a, 24b, and a plurality of spaced-apart openings 26 as shown in FIGS. 5 and 6. The openings 26 are dimensioned to operationally, frictionally and temporarily retain sensors A that have been inserted through the openings 26 as described herein. The openings 22 may be tapered, as shown in FIG. 6 to facilitate insertion of the sensors A through the openings 26 as described herein. For some applications, it may be desirable to taper the openings 26 toward both the upper surface 22 and the lower surface 24b. Preferably, the carrier 20 includes handles 28, guide elements 30, and a first positioning element or boss 32, as shown in FIG. 6. If desired, the carrier 20 may also include grips 31, as indicated by the dashed lines in FIG. 5, wherein the optional grips 31 extend upwardly from the upper surface 22.

The loading portion 12 includes a loading platform 38 and a rear wall 40 with a channel 42. The loading platform 38 has an upper surface 44 with a plurality of spaced-apart slots 46 which are spaced and dimensioned to correspond to the openings 26 of the carrier 20. Preferably, the centrally located slots 46 are dimensioned to accept two of the sensors A in a side by side relation, whereas the end slots 47 alongside the centrally located slots 46 are dimensioned to accept only one of the sensors A, as shown in FIG. 2. Part 48 of the loading platform 38 containing the slots 46, 47 may be fabricated integrally with the remainder of the loading portion 12, or fabricated separately so part 48 can be easily replaceable if necessary.

The loading portion 12 also includes a lower wall 52 having recesses 54, as schematically shown in FIG. 7. The recesses 54 are spaced to correspond to the slots 46 through the loading platform 38. The recesses 54 are dimensioned wherein the sensitive areas D of the test strips C can be displaced into the recesses 54, and wherein the distal ends G of the sheaths E cannot be so displaced. Rib 56 extends upwardly from the lower wall 52 and surrounds the recesses 54.

Spacing 58 between the lower wall 52 and the upper surface 44 of the loading platform 38 is dimensioned wherein, as lower surface 24b of the carrier 20 abuttingly engages the upper surface 44 of the loading platform 38, as described herein, with the distal ends G of the sheaths E of sensors A abutting the lower wall 52 and positioned over a respective recess 54, sensitive areas D of the test strips C can extend beyond the distal ends G of the sheaths E and into recesses 54 of the lower wall 52 to thereby expose predetermined lengths 60 of the sensitive areas D as schematically indicated in FIG. 8.

The testing portion 14 includes a container 66, a base 68, and a testing platform 70 having an upper surface 72. Preferably, the container 66 is cylindrically-shaped as shown in FIG. 3 and the base 68 is profiled, such as with a V-shaped inset 74 for example, to thereby enable a user to easily and accurately position the container 66 relative to the base 68. The testing platform 70 is mounted to the base 68 by an adjusting mechanism 76, such as a pair of vertically-oriented rods 78 for example, to thereby enable a user to selectively adjust spacing 80 of the upper surface 72 of the testing platform 70 relative to the surface 82 of a test specimen 84 contained in container 66. If desired, the testing platform 70 may include a clamping mechanism 85, such as knurled thumb screws in threaded bores as suggested in FIG. 12 for example, to thereby releasably secure the testing platform 70 relative to the rods 78.

For reliable testing purposes, it is important that only a specified length 86 of the sensitive areas D of the sensors A, as indicated in FIG. 8, be submerged in the test specimen 84 contained in the container 66. For example, the testing portion 14 may include a gauge device 88 depending from the testing platform 70 wherein the gauge device 88 has a distal end 90, as indicated in FIG. 12, that a user can visually use to align the surface 82 of the test specimen 84.

The testing platform 70 also includes a second positioning element 92 structured and configured to mate with the first positioning element 32 of the carrier 20 to thereby operatively align the sensors A, that are depending from the carrier 20 as described herein, with the container 66. It is foreseen that various other arrangements may be utilized to so operatively align the sensors A with the container 66.

The extracting portion 16 includes a comb-like element 102 having a plurality of spaced-apart fingers 104, the spacings of which correspond to respective openings 26 of the carrier 20 to operatively maintain the sensors A in a parallel relation. The extracting portion 16 also includes a bottom wall 106 and an end wall 108 with a plurality of studs 110 extending toward the comb-like element 102, each stud 110 having a distal end 112 and length 114. Part 116 of the end wall 108 containing the studs 110 may be fabricated integrally with the remainder of the extracting portion 16, or fabricated separately so part 116 can be easily replaceable if necessary.

The extracting portion 16 is structured and configured wherein spacing 118 between the comb-like element 102 and the distal ends 112 of the studs 110 is approximately equal to the distance which the sheaths E are displaced from their stowed configurations by the loading portion 12 as described herein. The length 114 of each stud 110 is approximately equal to the distance which the handling end B of each sensor A extends from lower surface 24b of the carrier 20 after the sensors A have been inserted through the openings 26 of the carrier 20 by the loading portion 12 as described herein.

For some applications of the present invention, it may be desirable to include a timing mechanism 124 which alerts the user when the allotted time for submersion of the sensors A in the test specimen 84 has transpired. The timing mechanism 124, as schematically shown in FIG. 15, may include a power source 126 such as an electrical circuit, a switch 128, a timer 130, and a signaling device 132 such as a light-emitting device 132 and/or a sound-emitting device 132 which alerts the user when the specified lengths 86 of the sensitive areas D of the test strips C have been soaked in the test specimen 84 for a desired length of time, forty-five seconds for example.

It is to be understood that the timing mechanism 124 may be a stand-alone device. Preferably, however, the timing mechanism 124 is arranged wherein contact between the carrier 20 and the upper surface 72 of the testing platform 70 of the testing portion 14 activates switch 128. Then, the user will be automatically alerted when the specified time has transpired.

As an example of an application of the present invention, such as when a urine specimen 84 has been taken from a suspect, the urine specimen 84 is placed in the container 66, the container 66 is properly positioned relative to the base 68 of the testing portion 14, and the gauge device 88 is used in conjunction with the adjusting mechanism 76 to properly space the testing platform 70 from the surface 82 of the test specimen 84.

A plurality of sensors A are selected for the test, one sensor for each of the drugs that may be found in the test specimen 84. By being able to selectively choose the desired individual sensors A, unnecessary waste is avoided by not having to use test strips designed to simultaneously test for several other drugs, some of which are not expected to be present in the test specimen 84.

The selected sensors A are then stood upright in the loading portion 12 with the sensors A arranged side by side in the double length slots 46 or singly in the end slots 47 as indicated in FIGS. 7-9, with the distal ends G of the sheaths E positioned over respective recesses 54 of the lower wall 52. Preferably, the loading portion 12 is structured wherein the sensors A tilt slightly rearwardly, such as approximately fifteen degrees from vertical for example, to thereby improve stability of sensors A prior to applying the carrier 20.

Then, the carrier 20 is positioned above the loading platform 38 of the loading portion 12. As the user presses downwardly on the handles 28 while sliding the guide element 30 along the channel 42 as indicated by the arrow designated by numeral 138 in FIG. 10, the distal ends G of the sheaths E are caused to bear against the lower wall 52 causing the handling ends B of the sensors A to be displaced through the openings 26 of the carrier 20. If desired, the spacing between guide posts 43 may be substantially equal to the width of channel 42 wherein guide element 30 sliding between guide posts 43 cooperatively provides added stability to guide element sliding along channel 42.

As the user continues to press downwardly on the handles 28, the sheaths E are caused to be telescopingly and slidingly displaced from their stowed configurations until the lower surface 24b of the carrier 20 abuttingly engages the upper surface 44 of the loading platform 38 and causing the predetermined lengths 60 of the sensitive areas D of the test strips C to be extended into the respective recesses 54.

Then, the carrier 22 is grasped by handles 28 and lifted from the loading platform 38 as indicated in FIG. 11. Friction between the handling ends B of sensors A and the carrier 20 retains the sensors A in their depending relation to the carrier 20 and friction between the sheaths E and their handling ends B retain the predetermined lengths 60 of the sensitive areas D in their extended relation below their respective sheaths E, as indicated in FIG. 11.

The carrier 20 with the sensors A depending therefrom is then lowered onto the testing platform 70 of the testing portion 14 whereat the second positioning element 92 mates with the first positioning element 32 thereby ensuring alignment of the sensors A with the container 66, as shown in FIG. 12. Spacing 80 ensures that only the specified lengths 86 of the sensitive areas D will be submerged in the test specimen 84 while the distal ends G of the sheaths E are spaced apart from the surface 82 of the test specimen 84 to thereby prevent unnecessary adherence of the test specimen 84 to the distal ends G of the sheaths E.

After the soak time of the specified lengths 86 has been completed, the carrier 20 is lifted from the testing platform 70 and lowered onto the comb-like element 102 such that the fingers 104 thereof are inserted between the sheaths E of the sensors A and the carrier 20 as shown in FIG. 13. As the carrier 20 is being displaced toward the end wall 108 of the extracting portion 16, the fingers 104 abut the proximal ends F of the sheaths E to telescopingly and slidingly return the sheaths E to their sensitive area-protecting stowed configurations whereupon the studs 110 abuttingly engage the handling ends B of the sensors A. If desired, a channel similar to channel 42 of the loading portion 42, may be formed in the bottom wall 106 of the extracting portion 16 to interface with an appropriate one of the guide elements 30 to thereby enhance stability of the carrier 20 as it is being displaced toward the end wall 108.

As the carrier 20 continues to be displaced toward and into abutting engagement with the end wall 108 of the extracting portion 16, the studs 110 eject the sensors A from the carrier 20 as shown in FIG. 14. Preferably, the end wall 108 is configured to receive the optional grips 31 so the grips 31 will not interfere with abutting engagement of the upper surface 22 of the carrier 20 with the end wall 108 of the extracting portion 16. Finally, the sensors A are carefully placed into an evidence bag or envelope to preserve and secure the evidence obtained from the test.

It is important to note that the sensitive areas D of the test strips A have been meticulously protected from contamination throughout the various steps of the testing procedures provided by the present invention.

It is foreseen that the present invention may be modified to utilize not only sensors configured to detect the presence of only one substance but to simultaneously or alternatively utilize sensors configured to concurrently detect the presence of several difference substances, similar to the Quicktox® provided by Branan Medical Corporation but with a slidably displaceable sheath as described herein.

Figure 16:
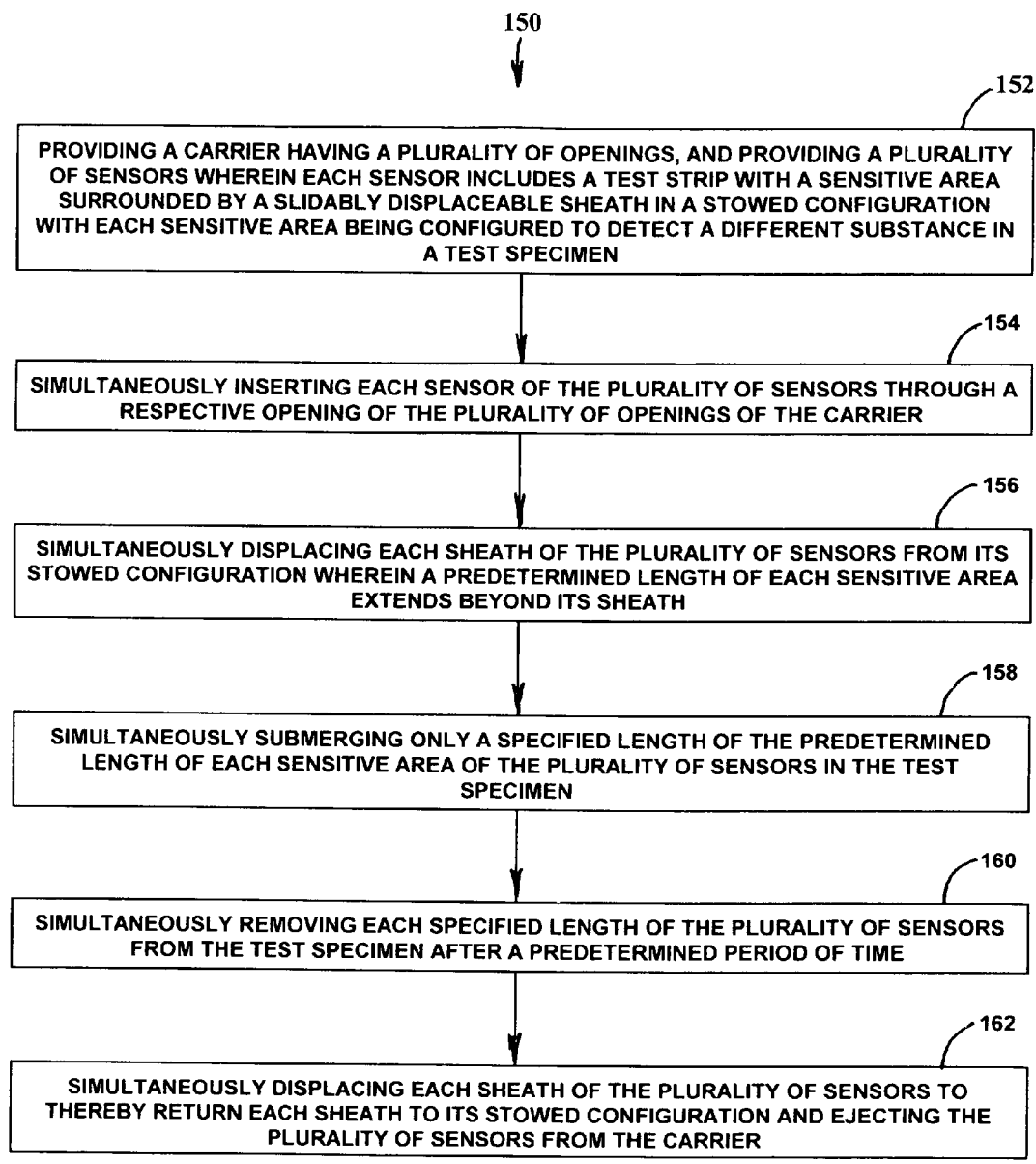
FIG. 16 is a schematic representation of a method for detecting a substance in a test specimen according to the present invention.

A method 150 of applying the present invention to detect a substance in a test specimen, as schematically represented in FIG. 16, includes the step 152 of providing a carrier 20 having a plurality of openings 26, and providing a plurality of sensors wherein each sensor includes a test strip with a sensitive area surrounded by a slidably displaceable sheath in a stowed configuration with each sensitive area being configured to detect a different substance in a test specimen; the step 154 of simultaneously inserting each sensor of the plurality of sensors through a respective opening 26 of the plurality of openings 26 of the carrier 20; the step 156 of simultaneously displacing each sheath of the plurality of sensors from its stowed configuration wherein a predetermined length 60 of each sensitive area extends beyond its sheath; the step 158 of simultaneously submerging only a specified length 86 of the predetermined length 60 of each sensitive area of the plurality of sensors in the test specimen; the step 160 of simultaneously removing each specified length 86 of the plurality of sensors from the test specimen after a predetermined period of time; and the step 162 of simultaneously displacing each sheath of the plurality of sensors to thereby return each sheath to its stowed configuration and ejecting the plurality of sensors from the carrier 20.

Summarizing, the present invention for conducting tests with a plurality of sensors for detecting the presence of certain substances in a test specimen taken from an individual enables a user working alone to simultaneously conduct tests on a test specimen with a plurality of sensors with sensitive areas, to simultaneously displace the sheaths of the plurality of sensors to thereby expose predetermined lengths of the sensitive areas thereof from their protective sheaths, to simultaneously submerge only specified lengths of the sensitive areas of the plurality of sensors in the test specimen while avoiding adherence of the test specimen to the sheaths, to alert the user when the sensitive areas of the plurality of sensors have been submerged in the test specimen for the time specified by the manufacturer of the sensors, and to simultaneously return the sheaths of the plurality of sensors to their stowed configurations to again protectively surround the sensitive areas thereof after completion of the tests on the test specimen, all while handling by the user occurs remotely from the sensitive areas.

It is to be understood that while certain forms of the present invention have been illustrated and described herein, it is not to be limited to the specific forms or connection of parts as described and shown.

What is claimed is:

1. An apparatus for utilizing at least one sensor having a test strip with a sensitive area surrounded by a slidably displaceable sheath in a stowed configuration wherein the sensitive area is configured to detect the presence of a certain substance in a liquid test specimen, the apparatus comprising:
   (a) a carrier having at least one opening,
   (b) a loading portion structured and configured to:
      (1) receive at least one sensor positioned upright therein wherein a user is enabled to cause said at least one sensor to be operatively and frictionally inserted through the at least one opening of the carrier, and
      (2) cause a sheath of said at least one sensor to be slidably displaced from a stowed configuration thereby exposing a predetermined length of a sensitive area of said at least one sensor;
   (c) a testing portion including:
      (1) a base,
      (3) a container alignable with the base, and
      (2) a testing platform adjustably mounted to the base and structured to support the carrier with said at least one sensor inserted therethrough wherein only a specified length of the predetermined length of the sensitive area of said at least one sensor is submerged in a test specimen contained in the container; and
   (d) an extracting portion structured and configured to receive the carrier with said at least one sensor inserted therethrough, the extracting portion including:
      (1) a comb-like element structured and configured to operatively displace and return the sheath of said at least one sensor to its stowed configuration, and
      (2) an end wall with studs structured and configured to operatively eject said at least one sensor from the carrier.

2. An apparatus for utilizing a plurality of sensors, each sensor having a test strip with a sensitive area surrounded by a slidably displaceable sheath in a stowed configuration wherein the sensitive area of each sensor is configured to detect the presence of a certain substance in a liquid test specimen, the apparatus comprising:
   (a) a carrier having a plurality of spaced-apart openings;
   (b) a loading portion structured and configured to:
      (1) receive a plurality of said sensors positioned upright therein wherein a user is enabled to cause the plurality of said sensors to be operatively and frictionally inserted through the plurality of openings of the carrier, and
      (2) cause sheaths of the plurality of said sensors to be slidably displaced from their stowed configurations thereby exposing predetermined lengths of sensitive areas of the plurality of said sensors;
   (c) a testing portion including:
      (1) a base,
      (2) a container alignable with the base, and
      (3) a testing platform adjustably mounted to the base and structured to support the carrier with the plurality of said sensors inserted therethrough wherein only specified lengths of the predetermined lengths of the sensitive areas of the plurality of said sensors are submerged in a test specimen contained in the container; and
   (d) an extracting portion structured and configured to receive the carrier with the plurality of said sensors inserted therethrough, the extracting portion including:
      (1) a comb-like element structured and configured to operatively displace the sheaths of the plurality of said sensors thereby returning the sheaths to their stowed configurations, and
      (2) an end wall with studs structured and configured to operatively eject the plurality of said sensors from the carrier.

3. An apparatus as described in claim 2, wherein the loading portion further comprises:
  (a) a loading platform having an upper surface and a plurality of slots corresponding to the plurality of openings of the carrier, and
  (b) a lower wall having a plurality of recesses corresponding to the plurality of slots of the loading platform wherein each sensor of the plurality of said sensors can be placed upright relative to a respective slot of the loading platform and a respective recess of the lower wall corresponding to that slot,
  (c) the upper surface of the loading platform being spaced from the lower wall wherein:
    (1) as the carrier is positioned above the plurality of said sensors placed upright in the loading portion and displaced downwardly, the plurality of said sensors are caused to be frictionally inserted through the openings of the carrier, and
    (2) as the carrier is further displaced downwardly until it abuttingly engages the upper surface of the platform, sheaths of the plurality of said sensors are displaced upwardly from their stowed configurations thereby operatively allowing sensitive areas of the plurality of said sensors to be extended into respective recesses of the lower wall thereby exposing predetermined lengths of the sensitive areas beyond their respective sheaths of the plurality of said sensors.

4. An apparatus as described in claim 2, wherein the testing portion further comprises a gauge element connected to the testing platform and configured to enable a user to adjust the testing platform relative to a surface of a test specimen contained in the container.

5. An apparatus as described in claim 4, wherein the gauge element is structured and configured to enable a user to adjust the testing platform to thereby prevent distal ends of said sheaths from touching or being submerged in said test specimen.

6. An apparatus as described in claim 2, wherein the extracting portion further comprises:
  (a) a comb-like element having a plurality of spaced-apart fingers corresponding to respective openings of the carrier, and
  (b) an end wall with a plurality of studs extending toward the comb-like element and corresponding to respective openings of the carrier,
  (c) wherein after the fingers of the comb-like element have been inserted between the carrier and the sheaths of the plurality of said sensors inserted through the openings of the carrier:
    (1) displacement of the carrier toward the end wall of the extracting portion until the studs abut the plurality of said sensors inserted through the openings of the carrier, whereupon the fingers of the comb-like element have slidingly displaced the sheaths returning them to their stowed configurations, and
    (2) continued displacement of the carrier toward the end wall until the carrier abuttingly engages the end wall thereby causing the studs to eject the plurality of said sensors from the openings of the carrier.

7. An apparatus as described in claim 2, further comprising a timing mechanism configured to alert a user when the allotted time for submersion of the specified lengths of the sensitive areas of the test strips in the test specimen has transpired.

8. An apparatus as described in claim 7, wherein the timing mechanism includes a switch which is automatically activated as the carrier contacts the testing platform when the specified lengths of the sensitive areas of the test strips are being submerged in the test specimen.

9. An apparatus for utilizing a plurality of sensors, each sensor having a test strip with a sensitive area surrounded by a slidably displaceable sheath in a stowed configuration wherein the sensitive area is configured to detect the presence of a certain substance in a liquid test specimen, the apparatus comprising:
  (a) a carrier having a plurality of spaced-apart openings;
  (b) a loading portion including:
    (1) a loading platform having an upper surface and a plurality of slots corresponding to the plurality of openings of the carrier, and
    (2) a lower wall having a plurality of recesses corresponding to the plurality of slots of the loading platform wherein each sensor of a plurality of said sensors can be placed upright relative to a respective slot of the loading platform and a respective recess of the lower wall corresponding to that slot,
    (3) the upper surface of the loading platform being spaced from the lower wall wherein:
      (A) as the carrier is positioned above the plurality of said sensors placed upright in the loading portion and displaced downwardly, the plurality of said sensors are caused to be frictionally inserted through the openings of the carrier, and
      (B) as the carrier is further displaced downwardly until it abuttingly engages the upper surface of the platform, sheaths of the plurality of said sensors are displaced upwardly from their stowed configurations thereby operatively allowing sensitive areas of the plurality of said sensors to be extended into respective recesses of the lower wall thereby exposing predetermined lengths of the sensitive areas beyond their sheaths of the plurality of said sensors;
  (c) a testing portion including:
    (1) a base,
    (2) a testing platform adjustably mounted to the base and structured to support the carrier with the plurality of said sensors inserted therethrough wherein only specified lengths of the predetermined lengths of the sensitive areas of the plurality of said sensors are submerged in a test specimen contained in the container;
    (3) a container alignable with the base, and
    (4) a gauge element configured to enable a user, in conjunction with the adjustable testing platform, to position the testing platform wherein only specified lengths of the sensitive areas of the plurality of sensors are operatively submerged in the test specimen;
  (d) an extracting portion structured and configured to receive the carrier with the plurality of said sensors inserted therethrough, the extracting portion including:
    (1) a comb-like element having a plurality of spaced-apart fingers corresponding to respective openings of the carrier, and
    (2) an end wall with a plurality of studs extending toward the comb-like element and corresponding to respective openings of the carrier,
    (3) wherein after the fingers of the comb-like element have been inserted between the carrier and the sheaths of the plurality of said sensors inserted through the openings of the carrier:
      (A) displacement of the carrier toward the end wall until the studs abut the plurality of said sensors whereupon the fingers of the comb-like element have slidingly displaced the sheaths returning them to their stowed configurations, and (B) continued displacement of the carrier toward the end wall until the carrier abuttingly engages the end wall thereby causing the studs to eject the plurality of said sensors from the openings of the carrier.

\* \* \* \* \*